US00PP25827P3

(12) United States Plant Patent
Maillard et al.

(10) Patent No.: US PP25,827 P3
(45) Date of Patent: Aug. 25, 2015

(54) APPLE TREE NAMED 'REGALYOU'

(50) Latin Name: ***Malus domestica* Borkh.**
Varietal Denomination: REGALYOU

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 215 days.

(21) Appl. No.: 13/815,926

(22) Filed: Mar. 18, 2013

(65) Prior Publication Data

US 2013/0263334 P1 Oct. 3, 2013

(30) Foreign Application Priority Data

Apr. 2, 2012 (QZ) ..... PBR 2012/0751

(51) Int. Cl.
*A01H 5/08* (2006.01)

(52) U.S. Cl.
USPC ..... Plt./161
CPC ..... *A01H 5/0875* (2013.01)

(58) Field of Classification Search
USPC ..... Plt./161
CPC ..... A01H 5/0875; A01H 5/08
See application file for complete search history.

*Primary Examiner* — Kent L Bell
(74) *Attorney, Agent, or Firm* — Westerman, Hattori, Daniels & Adrian, LLP

(57) ABSTRACT

A new and distinct variety of apple tree denominated 'REGALYOU' has fruits with large size and round shape, a red skin color, very firm, and with good eating quality; the fruit is further characterized by its good handling and storage qualities.

4 Drawing Sheets

Latin name of the genus and species of the plant claimed: *Malus domestica* Borkh.

Variety denomination: 'REGALYOU'.

This application claims priority of Community plant variety right No. 2012/0751 filed on Apr. 2, 2012 (Apr. 2, 2012) which is hereby incorporated by reference in its entirety.

BACKGROUND OF THE NEW VARIETY

1. Field of the Invention

In the field of plant genetics, we conduct an extensive and continuing plant-breeding program including the organization and reproduction of orchard trees, among which apple, peaches, nectarines, apricots, and cherries are exemplary. It was against this background of our activities that the present variety of apple tree was originated and reproduced by us in our experimental orchard located near Elne, Pyrénées Orientales, an administrative department of France.

2. Origin of the Variety

The present invention relates to a new a distinct variety of apple tree *Malus domestica* Borkh. which has been given the variety denomination 'REGALYOU'. This tree produces fruits with a long shelf life without alteration after harvesting, very good eating quality with a yellow flesh for fresh market in October in the Pyrénées Orientales department, France. Contrast is made to its parents 'RAKURAKU' apple tree (non patented) and to 'ARIANE 6407 RT' apple tree (non patented) for reliable description. 'REGALYOU' is a promising candidate for commercial success in that it produces very attractive fruits having a long shelf life.

The present new variety of apple tree (*Malus domestica* Borkh.) was developed by us in our experimental orchard located in France. 'REGALYOU' apple tree originated in a cultivated area of the South of France, in the Pyrénées-Orientales, an administrative department of France, where it was also tested. This zone also called Roussillon is subject to a Mediterranean climate. The winter is generally sweet and the summer is hot and dry. The total amount of cold hours lower than 7° C. (Celsius) varies from 600 hours to 1200 hours. The total amount of sunshine hours is an average of 2400 hours to 2800 hours per year. The prevailing wind is called "Tramontane": it dries the air and clear the sky from cloud but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen and the summer is dry with a few thunderstorms.

The 'REGALYOU' variety results from a pollinated cross between the 'RAKURAKU' apple tree (non patented) which was used as a seed parent and the 'ARIANE 6407 RT' apple tree (non patented) which was used as the pollen parent.

'REGALYOU' variety was provisionally designated, tested and genetically identified by a genetic profile under number 03.29E.43POM-ASF0720 and was registered at the Official Catalogue of the Agricultural Ministry of the French Republic on Nov. 27, 2011, under the number 4049385.

The 'REGALYOU' variety was obtained by hybridizing and propagated by grafting on a 'M9EMLA' (non-patented) rootstock trees. It has been determined to have unique tree and fruits characteristics making it worthy for commercial fresh fruits production. There are no known effects of the standard rootstock tree set forth above on the scion cultivar. Asexually propagated trees remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

SUMMARY OF THE NEW VARIETY

The new variety 'REGALYOU' produces fruits of large size, very firm and juicy, and with a luminous red color. The blooming period is medium for the variety, namely in the beginning of April. The maturity period is late or very late, generally during the first week of October in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at our site in the Elne Experiment Station, Route d'Alenya, La Prade de Mousseillous, 66200 ELNE, Pyrénées Orientales, South of France.

Figure 1:
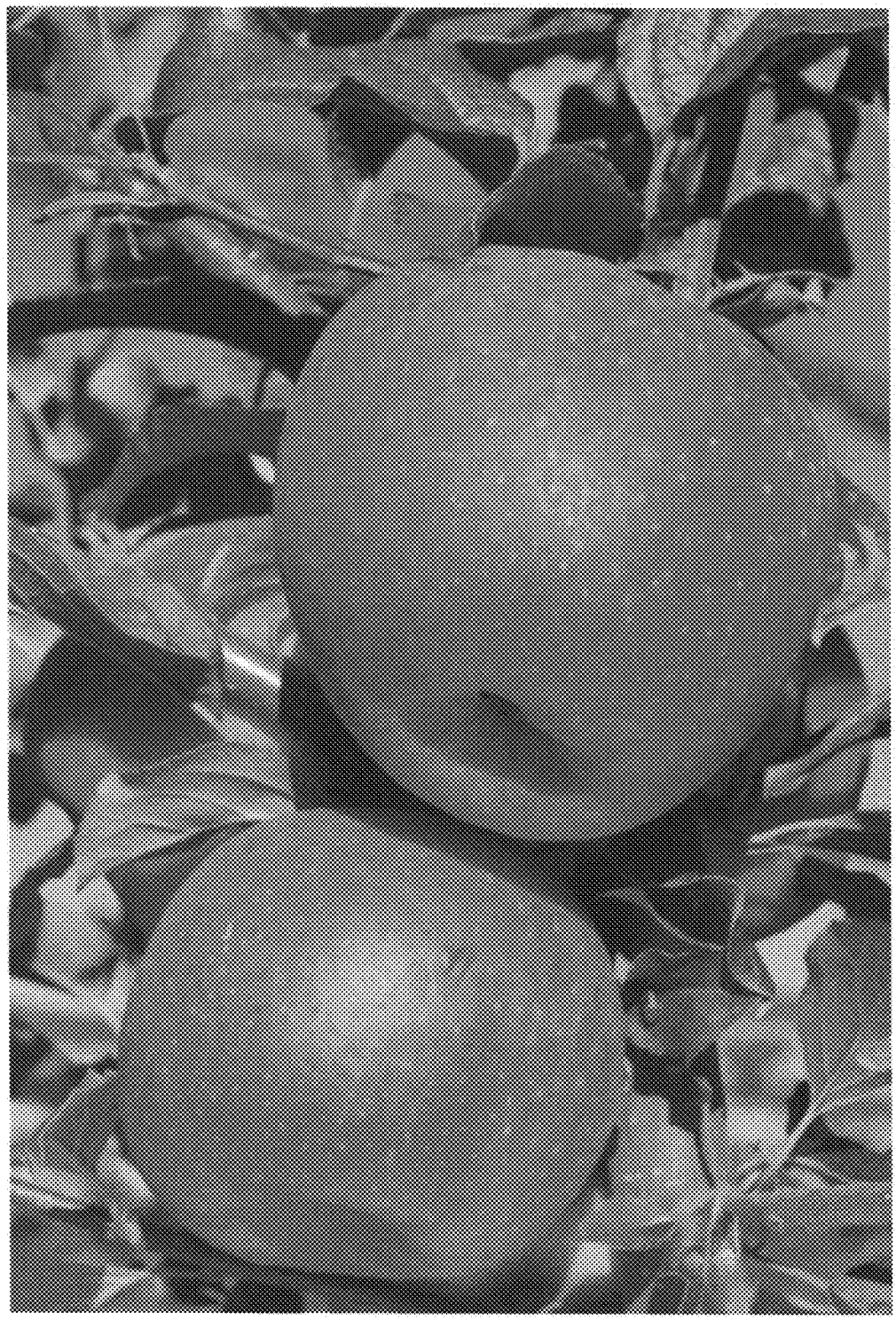
FIG. 1 is a color photograph which shows a branch of a tree of the new variety in an orchard, bearing fruits.
Figure 2:
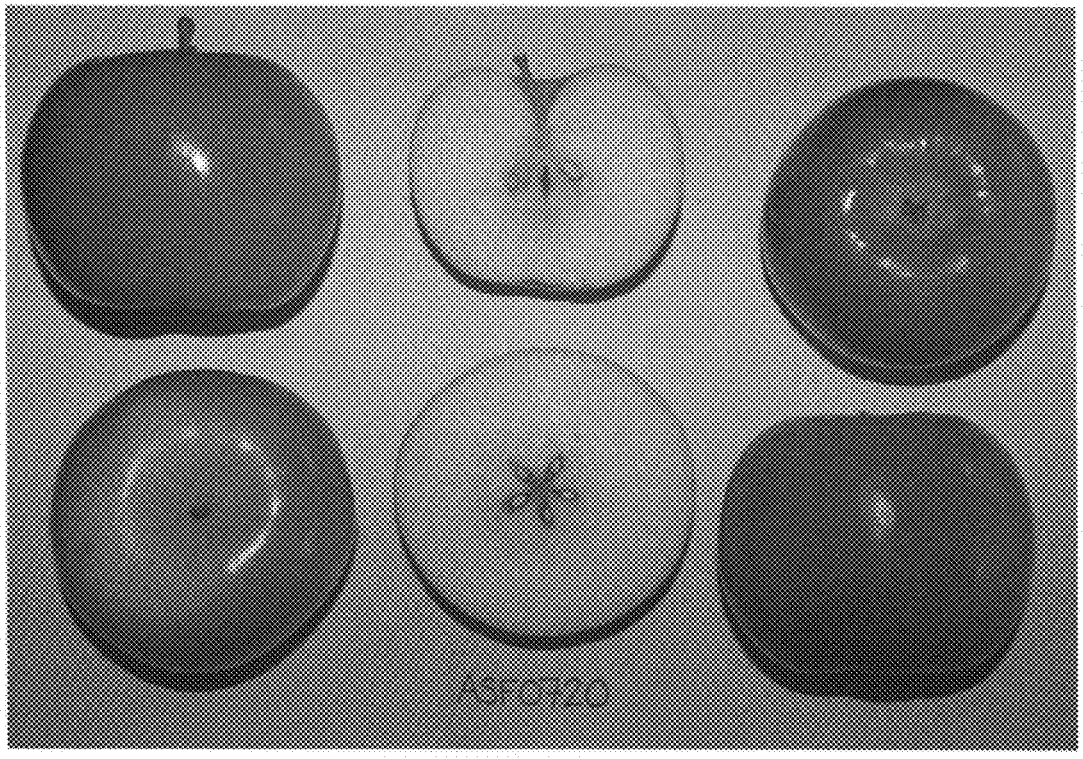
FIG. 2 is a color photograph which shows four whole fruits of the new variety, and a fifth fruit, cut in a half, for depicting the fruit flesh, the fruit core and the seeds of the new variety. The sixth fruit is cut in transverse cross section to show the locules.
Figure 3:
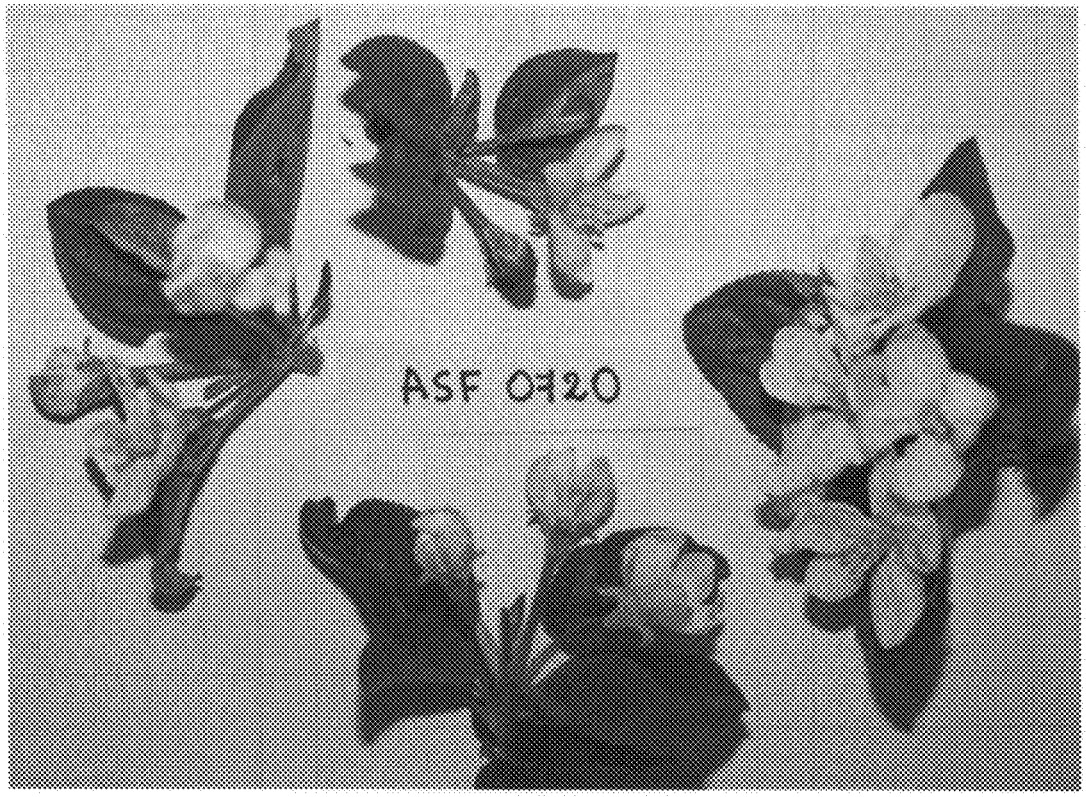
FIG. 3 shows typical flowers of 'REGALYOU' variety at blooming with some leaves for depicting the flower buds at different stages of development; and the reverse and side view of the flowers and the reproductive organs with petals removed, of the new variety.
Figure 4:
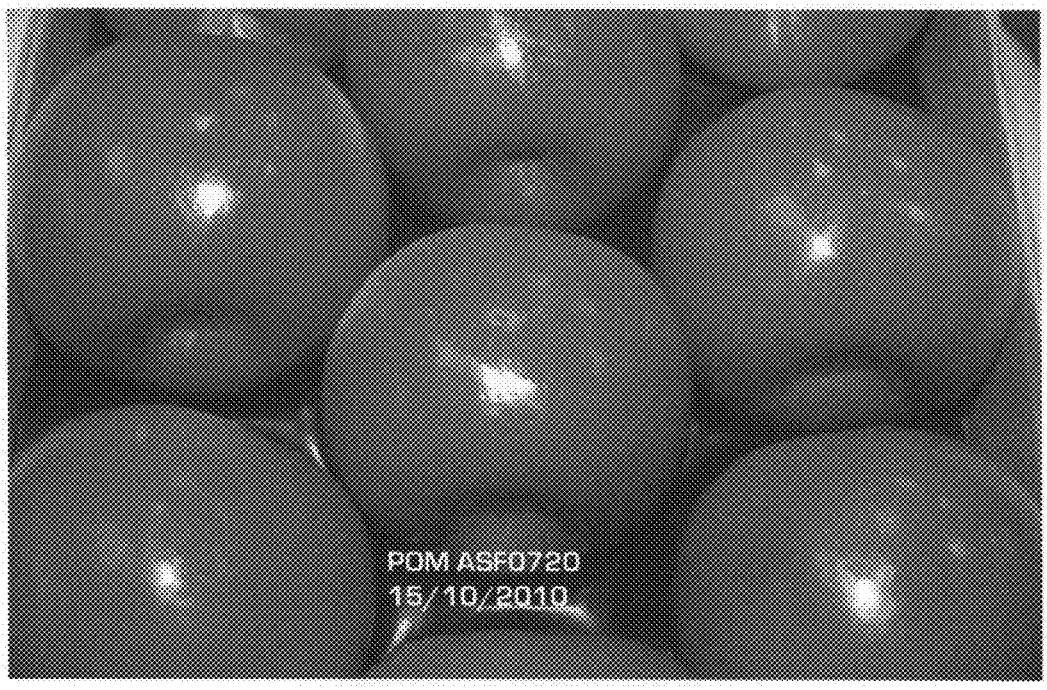
FIG. 4 is a color photograph that shows a close view of typical fruits of the new variety 'REGALYOU' at ripening time.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of apple tree, its flowers, foliage and fruit, as based on observations of specimens grown near Elne, South of France, with color in accordance with The R.H.S. Color Chart (Fourth Edition) provided by The Royal Horticultural Society of Great Britain.

The trees, flowers and fruits may vary in slight detail due to variations in soil type, cultural practices and climatic conditions.

The main characteristics of this new variety of sweet apple are a large fruit size with a color of skin considered red. The fruit flesh is yellow. The fruit is very firm.

The time of beginning of flowering is medium whereas the time of beginning of fruit ripening is considered late or very late.

In comparison to 'FUJI' apple tree variety (non-patented'), 'REGALYOU' apple tree blooms 3 days earlier and ripens approximately at the same time as 'FUJI'. The skin coloration of 'FUJI' variety is considered pink red covering 50 to 70% of skin whereas the skin coloration of 'REGALYOU' is luminous red on 80 to 90% of the fruit skin. The tree's ramification of 'REGALYOU' is denser than ramification of 'FUJI' apple tree. Flavor of 'REGALYOU' fruits is considered semi-sweet whereas 'FUJI' fruits show a sweet taste. Finally, 'REGALYOU' variety produces fruits regularly, without alternation, contrary to 'FUJI' variety, which may show an alternation in fruits production.

The female parent of the new variety, which is denominated 'RAKURAKU' (non-patented) is a striated mutant of the 'FUJI' variety. In comparison with the apple tree 'RAKURAKU', the present variety 'REGALYOU' have a tree's ramification denser compared to ramification of 'RAKURAKU', which is considered very weak or even insufficient. The fruits productivity of 'REGALYOU' is higher than 'RAKURAKU' productivity, considered medium because of its susceptibility to alternate production. Fruits of 'RAKURAKU' are round with few bumps whereas 'REGALYOU' fruits are regular-shaped. The color of 'REGALYOU' fruits skin is also more interesting, with a luminous red that covers 80% to 90% of the fruit skin on a wash red orange background; in comparison, fruit skin of 'RAKURAKU' is pink red on a greenish yellow background. Fruits flesh of 'REGALYOU' apple tree is not fibrous, contrary to 'RAKURAKU' fruits flesh, and 'REGALYOU' taste is slightly acid and aromatic.

The male parent of the new variety 'ARIANE 6407 RT' (non-patented) was obtained by INRA® and is resistant to common species of the fungus named *Venturia inaequalis*. 'REGALYOU' tree's ramification is higher than 'ARIANE 6407 RT' tree's ramification, which is considered medium or insufficient. The level of production of the new variety is similar to those of 'ARIANE 6407 RT' and considered regular without susceptibility to alternate production. 'REGALYOU' fruits don't include lenticels, in comparison with 'ARIANE 6407 RT' fruits. Moreover, 'REGALYOU' fruits are larger than 'ARIANE 6407 RT' fruits.

DETAILED DESCRIPTION

Referring more specifically to the pomological details of this new and distinct variety of apple tree, the following has been observed on trees on their third growing season (second year of production) under the ecological conditions prevailing at the orchards located near the town of Elne, Pyrénées-Orientales, an administrative department of France.

All observations have been done on rootstock cultivar. The rootstock was a 'M9EMLA' (non-patented) tree. All major color code designations are by reference to The R.H.S. Color Chart (Fourth Edition) provided by The Royal Horticultural Society of Great Britain.

TREE

Generally: The first year the apple tree is generally cut at 2.80 meters height. The length in one year for each lateral shoot varies from 0.60 meters to 0.80 meters. We are cutting the apple trees during the second year to a height of 2.50 meters. The form of the apple trees is cylindrical and the diameter is limited to 1 meter.

*Size*.—Medium to high as compared to other commercial apple cultivars. The tree size the first year was approximately 2.80 meters. The tree was pruned during each following dormant season to a height of approximately 2.50 meters. Current season's shoots growth could reach 0.80 meters. So the tree size from the second year (second and next years) reached a final height of 3.10 to 3.30 meters with current seasons shoots length comprised.

*Spread*.—Approximately 1.0 meter with a cylindrical shape. The whole orchard was oriented to a central leader organization, with tree lines spaced of 4.0 meters and trees spaced of 1 meter in a same tree line.

*Vigor*.—Strong, tree growth reaching 0.60 to 0.80 meters the first growing season.

*Productivity*.—Good to very good productivity, every year and without alternation. The new variety produces adequate fruit set annually on a regular basis. The number of the fruit set varies with the prevailing climatic conditions and cultivar practices employed during the bloom period, and is therefore not distinctive of the present variety.

*Bearer*.—Very regular every year.

*Type*.—Ramified.

*Habit*.—Spreading.

*Form*.—Naturally semi-spread to semi-upright.

*Hardiness*.—Hardy in all stone fruit growing areas of France and especially where the chilling requirement is between 350 and 1200 hours. No injury with temperatures as low as −12° C. in winter. Good resistance to late frosts.

Trunk:

*Size*.—Medium. Measured between 28.0 and 32.0 millimeters at 10.0 centimeters above the graft union.

*Bark texture*.—Smooth to rough, due to the lenticels.

*Lenticels*.—Medium number of lenticels. The number of lenticels reaches 2 to 5 lenticels per $cm^2$.

*Lenticels color*.—Color of lenticels is considered grey orange (RHS Greyed Orange 164 A to RHS Greyed Orange 164 B).

*Bark color*.—Grey brown (RHS Grey Brown N199 A or RHS Grey 201 A).

Branches:

*Diameter*.—Branches at the 2nd growing season have an average diameter of 10.0 to 22.0 millimeters.

*Length*.—Between 25.0 and 100.0 centimeters.

*Surface texture*.—Smooth to rough, due to lenticels.

*Lenticels*.—Lenticels on branches at the 2nd growing season are medium with a diameter between 1.5 and 2.0 millimeter and a round to slightly elongated shape.

*Color*.—Branches are brown (RHS Brown 200 D).

*Crotch angles*.—Between 80 degrees and 90 degrees from the supporting branch. This particular characteristic is not considered distinctive of the variety, however.

*Internode*.—Generally from 19.0 millimeters to 24.0 millimeters length.

Current season shoots:

*Diameter*.—Average diameter from 6.0 to 12.0 millimeters.

*Length*.—Between 10.0 and 100.0 centimeters.

*Surface texture*.—Smooth to rough, due to lenticels.

*Lenticels*.—Considered generally small in size, with a diameter between 0.5 and 1.0 millimeter and a round to slightly elongated shape.

*Crotch angles*.—Between 60 degrees and 70 degrees from the supporting branch. This particular characteristic is not considered distinctive of the variety, however.

*Internode*.—Generally from 19.0 millimeters to 24.0 millimeters length.

*Color*.—New growth is brown (RHS Brown 200 A to RHS Brown 200 B).

LEAVES

*Size*.—Medium for the species. The ratio leaf length/leaf width is 1.93.

*Length*.—Approximately 120.0 millimeters with leaf petiole.

*Width*.—Approximately 62.3 millimeters.

*Leaf form*.—Ovoid.

*Apex*.—Pointed (approximately 40°).

*Base*.—Round-shaped.

*Margins*.—Crenate.

*Surface texture*.—Medium to low pubescence on lower surface of the leaves. No pubescence on upper surface.

Leaf color:

*Upper leaf surface*.—Green (RHS GREEN 137 A or RHS YELLOW GREEN 147 A).

*Lower surface*.—Considered yellow green (RHS YELLOW GREEN 147 B or RHS YELLOW GREEN 148 B).

*Leaf venation*.—Pinnately veined, fairly alternate.

Leaf petioles:

*Length*.—About 26.0 to 30.0 millimeters.

*Diameter*.—About 2.7 to 3.0 millimeters.

*Color*.—Upper surface light green (RHS YELLOW GREEN 146 B to 146 C). Lower surface light green (RHS YELLOW GREEN N144 A or RHS YELLOW GREEN 151 A).

*Grooves on petiole*.—Prominent.

Leaf stipules:

*Generally*.—Two stipules are observed.

*Length*.—Between 9.0 to 11.0 millimeters.

*Width*.—Between 3.0 to 4.0 millimeters.

*Color*.—Leaf stipules show the same color as whole leaf color. Upper stipules surface is considered green (RHS GREEN 137 A or RHS YELLOW GREEN 147 A) and lower stipules surface is yellow green (RHS YELLOW GREEN 147 B or RHS YELLOW GREEN 148 B).

Spurs:

*Length*.—Between 4.0 and 5.0 millimeters.

*Width*.—Between 4.0 and 5.0 millimeters.

*Color*.—Brown (RHS BROWN 200A).

*Position on the branch*.—Apprimed.

*Length between two spurs*.—Between 18.0 and 22.0 millimeters.

FLOWERS

Flower buds:

*Generally*.—At pre-floral stage of development, the floral bunches are made up with 3 to 5 floral buds having a conic shape with a round tip. Their form is evolving until blooming, with variable dimensions. Just before blooming, floral buds are approximately 11.0 millimeters in diameter and approximately 6.0 millimeters long.

*Color*.—This characteristic is dependent upon the proximity to bloom. At pre-floral stage of development, the bottom of the flowers buds, or calyx formed by sepals, is of green color (RHS GREYED GREEN 194 B to RHS GREYED GREEN 194 C). The corolla formed by petals, is generally pink violet (RHS GREYED PURPLE 186 B to RHS GREYED PURPLE 186 C).

*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom*.—Generally early in April. The first bloom was observed on April 5 until April 15, 2008.

*Blooming time*.—Considered medium in relative comparison to other commercial apple cultivars grown in the Pyrénées-Orientales department, France. The date of bloom varies slightly with climatic conditions and cultural practices.

*Blooming period*.—Average 10 days. This characteristic varies slightly with the prevailing climatic conditions.

*Flower type*.—The variety is considered to have a showy type flower.

*Flower size*.—Considered large. Average diameter of the corolla is between 22.0 and 28.0 millimeters when totally opened.

*Flower bud frequency*.—Generally 5 to 6 flower buds appear per node.

Petal:

*Size*.—Considered medium for the species.

*Length*.—Generally about 12.3 millimeters.

*Width*.—Generally about 8.2 millimeters.

*Petal form*.—Round, elongated, with slightly curved margins. The petal tip is also round.

*Petal base*.—Round.

*Petal margins*.—Slightly curved.

*Petal count*.—Nearly always 5.

*Petal texture*.—Smooth and soft.

*Petal color*.—The inner surface is considered white (RHS WHITE 155 D) and the outer surface is pink violet (RHS GREYED PURPLE 186 B to RHS GREYED PURPLE 186 C).

*Fragrance*.—Soft.

Petal apex:

*Generally*.—The petal apices are generally round shaped.

Flower pedicel:

*Length*.—Average length between 20.0 to 25.0 millimeters.

*Diameter*.—Average 1.7 millimeters.

*Color*.—Light green (RHS YELLOW GREEN 146 C to RHS YELLOW GREEN 146 D).

Calyx:

*Color*.—The calyx is green (RHS GREEN 138 A).

Sepals:

*Size*.—Usually considered medium.

*Number*.—Generally 5 sepals per flower.

*Sepal form*.—Triangular.

*Apex*.—Pointed, narrow and hooked.

*Margins*.—Smooth, slightly pubescent.

*Color*.—Both surfaces of the sepals are green (RHS GREYED GREEN 194 B to RHS GREYED GREEN 194 C).

Stamens:

*Average number of stamens per flower*.—Approximately 15 stamens per flower.

*Color*.—White (RHS WHITE 155 C).

Pollen:

*Generally*.—Present.

*Color*.—Pollen has a yellow color (RHS GREEN YELLOW 1 C). The variety could be pollinated with viable pollen from another variety such as 'FUJI' apple tree or 'GOLDEN' apple tree, these varieties having approximately the same time of blooming as 'REGALYOU'.

Filaments:

*Size*.—Variable in length, approximately between 4.0 and 12.0 millimeters in length.

*Color*.—Considered as white (RHS WHITE 155 D).

Pistil:

*Size*.—Medium for the variety.

*Length*.—Approximately from 4.0 to 5.0 millimeters long and 0.8 millimeter wide.

*Color*.—Considered pale green (RHS YELLOW GREEN 149 B to RHS YELLOW GREEN 149 C).

Style:

*Length*.—Approximately 4.0 to 5.0 millimeters.

*Width*.—Approximately 0.5 millimeter.

*Color*.—Light green (RHS YELLOW GREEN 151 A).

FRUITS

*Maturity when described*.—Very firm at maturity.

*Date of first picking*.—Oct. 1, 2008, varies slightly with climatic conditions.

*Date of last picking*.—Oct. 10, 2008 varies slightly with climatic conditions. The harvest is generally performed in two runs.

*Ripening period*.—Generally during the first week of October.

*Amount of fruits per tree*.—Between 80 and 100 fruits per tree for an orchard containing 2500 trees by hectare.

Size:

*Generally*.—Considered large, with a homogeneous size between them for 80% of fruits.

*Average transversal diameter*.—About 75.0 to 85.0 millimeters.

*Average axial diameter*.—About 78.0 to 80.0 millimeters.

*Typical weight*.—Generally about 300.0 grams. This characteristic is highly dependent upon the prevailing cultural practices, and therefore is not particularly distinctive of the variety.

Fruit form:

*Generally*.—Obloid, round to slightly flatten in shape.

*Fruit suture*.—Wide mouthed, extending from the base to the apex. No apparent callousing or stitching exists along the suture line. Without mucrons.

Fruit stem:

*Length*.—Between 20.0 and 25.0 millimeters.

*Diameter*.—About 3.0 millimeters.

*Color*.—Light green (RHS YELLOW GREEN 146 C to RHS YELLOW GREEN 146 D or RHS YELLOW GREEN 152 D).

Stem cavity:

*Form*.—Obtuse.

*Depth*.—Average depth 18.0 millimeters.

*Width*.—Between 12.0 and 17.0 millimeters.

Fruit eye basin:

*Form*.—Round and symmetrical, slightly wide-mouthed.

*Depth*.—Average depth 14.0 millimeters.

*Width*.—Between 20.0 and 25.0 millimeters.

Calyx:

*Generally*.—Small and symmetrical.

*Form*.—Closed or very slightly opened.

*Texture*.—Slightly pubescent.

Fruit skin:

*Thickness*.—Considered medium thick.

*Texture*.—Smooth.

*Tendency to crack*.—None.

Lenticels:

*Number*.—About 3 lenticels per $cm^2$ of fruit skin.

*Size*.—Small.

*Form*.—Round.

*Diameter*.—Approximately 0.8 to 1.0 millimeter.

*Color*.—Orange brown (RHS GREYED ORANGE 164 D).

Skin color:

*Over color*.—This over color is a considered orange red to red (RHS GREYED PURPLE 185 A or RHS RED 46 A) and covers approximately 80% to 90% of fruit skin.

*Striping*.—Absent.

*Ground color*.—The ground color is RHS GREYED RED 181 C on more or less 20% of the fruit skin.

Flesh:

*Texture*.—Very crunchy, melty.

*Fibers*.—No fibers.

*Firmness*.—Very firm. The measure of pressure shows a value between 7.0 to 7.5 $kg/cm^2$ with a penetrometer having a diameter of 11.3 millimeters.

*Aroma*.—Present.

*Juice*.—Large amount, very juicy.

*Brix*.—Superior to 15.0 degrees until 17.0 degrees, varies slightly with amount of fruit per tree and climatic conditions.

*Color*.—Yellow (RHS YELLOW 8 D) at ripening time.

Fruit core:

*Form*.—Generally symmetrical.

*Stamen bundles*.—Generally ten per fruit, approximately 0.8 millimeter diameter.

*Locules area*.—Flattened and slightly elongated.

*Calyx tubes*.—Narrow.

*Fruit eye basin*.—About 25.0 to 27.0 millimeters in depth, including style.

*Size*.—Medium for the variety.

*Core line* (*styles*).—Shallow.

*Stamens*.—Visible.

*Axillary cavity*.—Semi-narrow.

*Locules*.—Depth of locules walls is approximately 1.0 millimeter, locules length is about 30.0 millimeters and locules width is between 16.0 and 20.0 millimeters.

*Aperture of locules*.—Closed.

Seeds:

*Count*.—Generally 8 to 10 seeds are present.

*Number of seeds per locule*.—Usually 1 or 2 seeds.

*Length*.—Approximately 8.0 millimeters.

*Width*.—Approximately 5.0 millimeters.

*Form*.—Ovoid shape.

*Color*.—Brown (RHS BROWN 200 A to RHS BROWN 200 B).

Use: Dessert, fresh products, fruit juice.

*Market*.—Local and long distance. On the tree fruits can stay 10 days while keeping good gustative qualities. The lifetime after picking is also good.

Keeping quality: Good, held well for 3 to 4 months in cold storage at 1° C. and maintained good appearance and eating quality. At room temperature (18° C.), fruits are well preserved for about 2 months.

Shipping quality: Good, showed minimal bruising or scarring during picking, packing and shipping trials.

Plant/fruit disease resistance/susceptibility: In our growing conditions, no particular symptom was noticed.

*Robustness to winter*.—Very good for trees and flower buds.

*Tolerance to dryness*.—Good.

The present new variety of apple tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of apple tree, substantially as illustrated and described, characterized by its fruit and especially by its large size and round shape, its red skin color, its firmness, and eating quality; the fruit is further characterized by its good handling and storage qualities.

* * * * *